(12) United States Patent
Chen et al.

(10) Patent No.: US 10,679,740 B2
(45) Date of Patent: Jun. 9, 2020

(54) SYSTEM AND METHOD FOR PATIENT PRIVACY PROTECTION IN MEDICAL IMAGES

(71) Applicant: THE CHINESE UNIVERSITY OF HONG KONG, Shatin, N.T., Hong Kong SAR (CN)

(72) Inventors: Weitian Chen, Hong Kong SAR (CN); Ke Gan, Chengdu (CN)

(73) Assignee: THE CHINESE UNIVERSITY OF HONG KONG, Shatin (HK)

(*) Notice: Subject to any disclaimer, the term of this patent is extended or adjusted under 35 U.S.C. 154(b) by 101 days.

(21) Appl. No.: 16/006,663

(22) Filed: Jun. 12, 2018

(65) Prior Publication Data

US 2019/0378607 A1 Dec. 12, 2019

(51) Int. Cl.
*G06K 9/00* (2006.01)
*G16H 30/20* (2018.01)
(Continued)

(52) U.S. Cl.
CPC ......... *G16H 30/20* (2018.01); *G06F 21/6245* (2013.01); *G06F 21/6254* (2013.01);
(Continued)

(58) Field of Classification Search
CPC ........... G06K 9/00201; G06K 9/00221; G06K 9/00228; G06K 9/00234; G06K 9/34; G06K 9/342; G06K 9/38; G06K 2009/00953; G06K 2209/05; G06T 5/002; G06T 5/20; G06T 5/30; G06T 7/0012; G06T 7/10; G06T 7/11; G06T 7/12; G06T 7/136;
(Continued)

(56) References Cited

U.S. PATENT DOCUMENTS 9,633,482 B2 * 4/2017 Ashmole .................. G06T 7/73
10,332,238 B2 * 6/2019 Wiemker .................. G06T 7/11
10,452,812 B2 * 10/2019 Gogin .................. G06F 19/321

OTHER PUBLICATIONS

Francois Budin, Donglin Zeng, Arpita Ghosh and Elizabeth Bullitt, "Preventing facial recognition when rendering MR images of the head in three dimensions", Elsevier, Medical Image Analysis, vol. 12, Issue 3, Jun. 2008, pp. 229-239 (Year: 2008).*
(Continued)

*Primary Examiner* — Eric Rush
(74) *Attorney, Agent, or Firm* — Kilpatrick Townsend & Stockton LLP

(57) ABSTRACT

Systems and methods for de-identification of medical images can be applied to medical images acquired using various techniques. A 3D medical image can be analyzed to generate an image mask that partitions the image into a foreground region and a background region. From the image mask, a "skin surface" can be reconstructed based on the boundary between the foreground region and the background region. The image mask can be modified, e.g., by moving a randomly-selected subset of the voxels from the foreground region to the background region so that the shape of the skin surface is altered, thus obscuring patient-identifying features. The original medical image can be modified by changing the intensity of voxels in the background region while preserving the original intensity of voxels in the foreground region.

29 Claims, 15 Drawing Sheets

(10 of 15 Drawing Sheet(s) Filed in Color)

(51) Int. Cl.
| | |
|---|---|
| G06T 19/20 | (2011.01) |
| G06T 7/155 | (2017.01) |
| G06T 7/194 | (2017.01) |
| G06T 5/20 | (2006.01) |
| G16H 10/60 | (2018.01) |
| G06T 5/00 | (2006.01) |
| G06F 21/62 | (2013.01) |
| G16H 30/40 | (2018.01) |
| G06T 7/00 | (2017.01) |

(52) U.S. Cl.
CPC .............. *G06T 5/002* (2013.01); *G06T 5/20* (2013.01); *G06T 7/0012* (2013.01); *G06T 7/155* (2017.01); *G06T 7/194* (2017.01); *G06T 19/20* (2013.01); *G16H 10/60* (2018.01); *G16H 30/40* (2018.01); *G06K 2009/00953* (2013.01); *G06T 2207/10028* (2013.01); *G06T 2207/10088* (2013.01); *G06T 2207/30004* (2013.01); *G06T 2219/2021* (2013.01)

(58) Field of Classification Search
CPC ......... G06T 7/155; G06T 7/194; G06T 19/00; G06T 19/20; G06T 2207/10028; G06T 2207/10072; G06T 2207/10081; G06T 2207/10088; G06T 2207/10136; G06T 2207/30004; G06T 2207/30016; G06T 2207/30088; G06T 2219/2021; G16H 10/60; G16H 30/00; G16H 30/20; G16H 30/40; G06F 19/32; G06F 19/321; G06F 21/60; G06F 21/6245; G06F 21/6254; H04L 2209/04; H04L 2209/08; H04L 2209/16; H04L 2209/42; G08B 13/19686; H04N 1/38; H04N 1/387; H04N 1/3872; H04N 1/407; H04N 1/4072; H04N 1/44; H04N 1/448; H04N 1/4493
USPC ........ 382/100, 115–118, 128, 131, 132, 154, 382/173, 199, 203, 224, 256, 257, 276, 382/282, 283; 705/2, 3; 726/26; 345/419, 424, 428, 581, 619, 625, 626, 345/647
See application file for complete search history.

(56) References Cited

OTHER PUBLICATIONS

Vladimir S. Fonov and Louis D. Collins, "BIC Defacing Algorithm", bioRxiv 275453, doi.org/10.1101/275453, Mar. 2, 2018, pp. 1-7 (Year: 2018).*

Shaswati Row and Pradipta Maji, "A Simple Skull Stripping Algorithm for Brain MRI", IEEE, 2015 Eighth International Conference on Advances in Pattern Recognition (ICAPR), 2015, pp. 1-6 (Year: 2015).*

Achanta, et al., Süsstrunk. Slic superpixels. No. EPFL-REPORT-149300. 2010.

Achanta, et al. "SLIC superpixels compared to state-of-the-art superpixel methods." IEEE transactions on pattern analysis and machine intelligence 34, No. 11 (2012): 2274-2282.

Bischoff-Grethe, et al. "A technique for the deidentification of structural brain MR images." Human brain mapping 28, No. 9 (2007): 892-903.

Chen, et al. "Implications of surface-rendered facial CT images in patient privacy." American Journal of Roentgenology 202, No. 6 (2014): 1267-1271.

Chen, Weitian. "Artifacts correction for T1rho imaging with constant amplitude spin-lock." Journal of Magnetic Resonance 274 (2017): 13-23.

Gan, Ke. "Automated segmentation of the lateral ventricle in MR images of human brain." In Digital Signal Processing (DSP), 2015 IEEE International Conference on, pp. 139-142. IEEE, 2015.

Gan, Ke. "Automated localization of anatomical landmark points in 3D medical images." In Digital Signal Processing (DSP), 2015 IEEE International Conference on, pp. 143-147. IEEE, 2015.

Gan, Ke, and Daishen Luo. "Facial De-Identification in Multimodality MR Images." Transactions of Japanese Society for Medical and Biological Engineering 51, no. Supplement (2013): R-238.

IXI Dataset, retrieved at http://brain-development.org, Imperial College London, 2 pages.

Kim, et al. "Improved simple linear iterative clustering superpixels." In Consumer Electronics (ISCE), 2013 IEEE 17th International Symposium on, pp. 259-260. IEEE, 2013.

Kyme, et al. "Refraction-compensated motion tracking of unrestrained small animals in positron emission tomography." Medical image analysis 16, No. 6 (2012): 1317-1328.

Schimke, et al. "Neuroimage data sets: rethinking privacy policies." In Proceedings of the 3rd USENIX conference on Health Security and Privacy, pp. 301-308. USENIX Association, 2012.

Schimke, et al. "Quickshear Defacing for Neuroimages." In HealthSec. 2011.

Smith, Stephen M. "Fast robust automated brain extraction." Human brain mapping 17, No. 3 (2002): 143-155.

Villanueva-Meyer, et al. "Differentiation of brain tumor-related edema based on 3D T1rho imaging." European journal of radiology 91 (2017): 88-92.

* cited by examiner

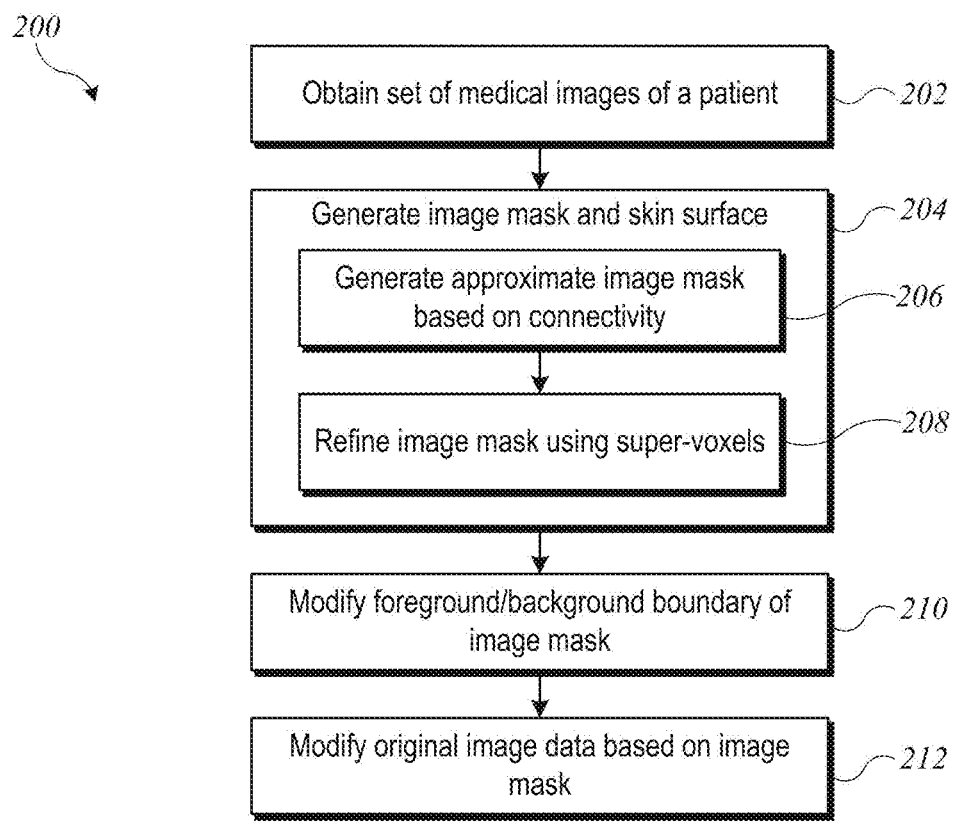

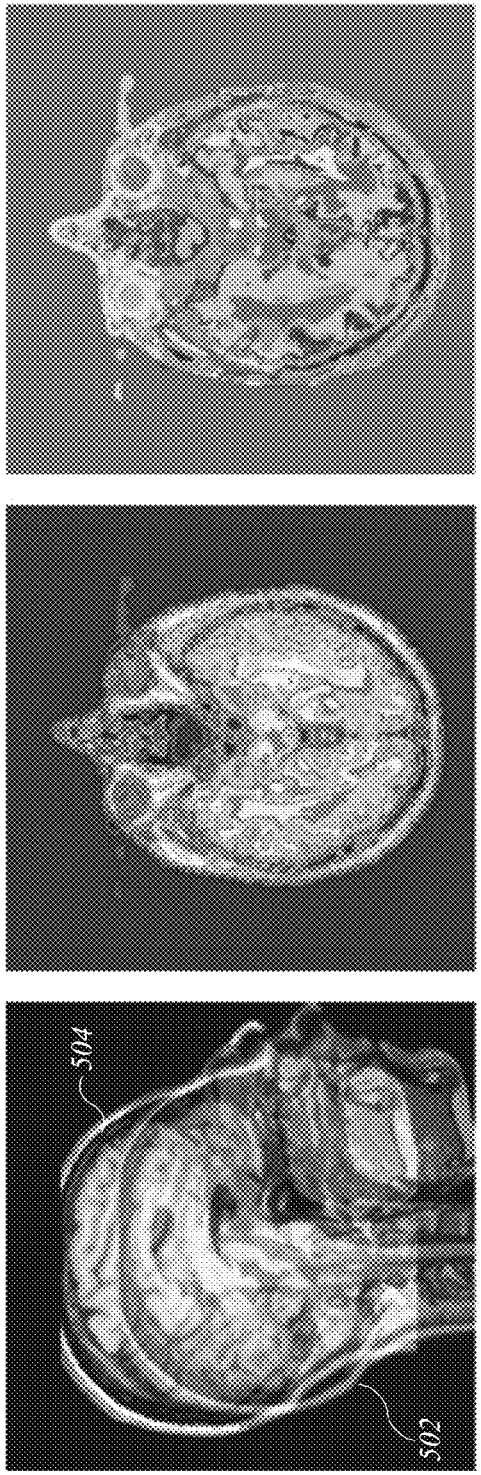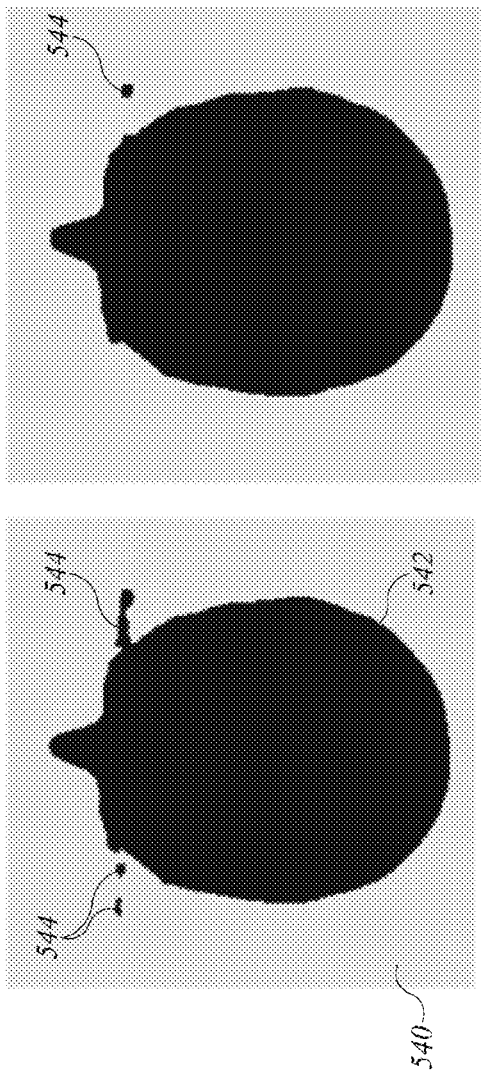
FIG. 5C
FIG. 5B
FIG. 5A
FIG. 5E
FIG. 5D

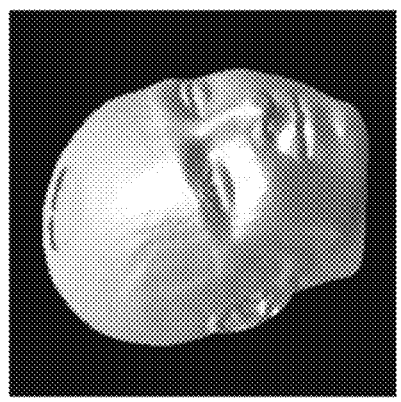
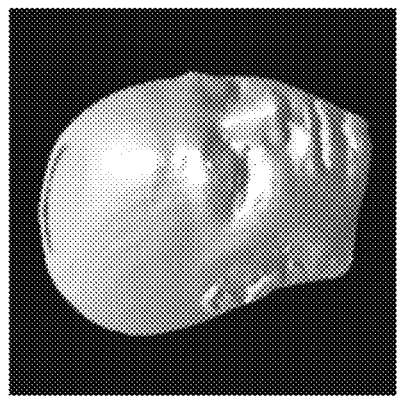
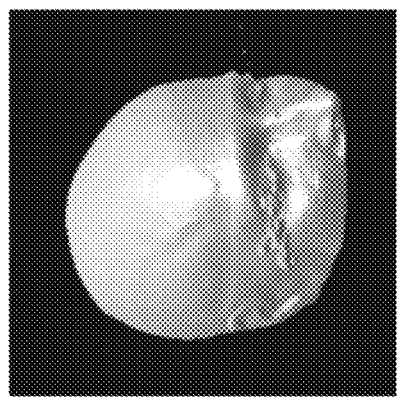
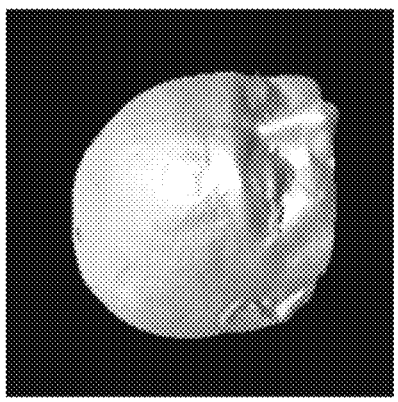
FIG. 15A  FIG. 15B  FIG. 15C  FIG. 15D
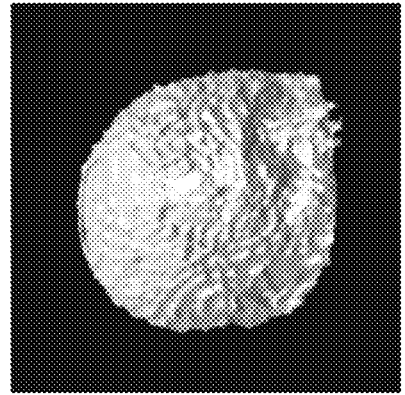
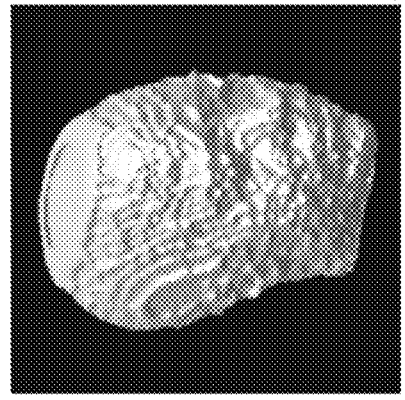
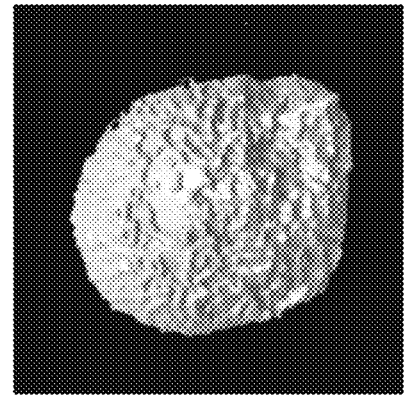
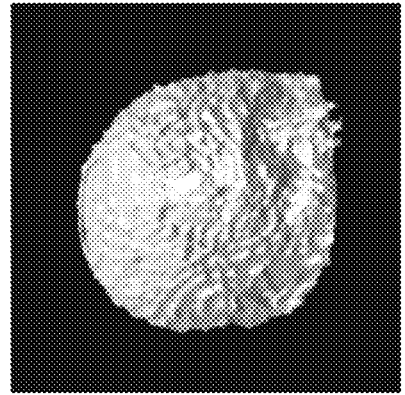
FIG. 16A  FIG. 16B  FIG. 16C  FIG. 16D

SYSTEM AND METHOD FOR PATIENT PRIVACY PROTECTION IN MEDICAL IMAGES

BACKGROUND

The present disclosure relates generally to data privacy for medical images and in particular to systems and methods for obscuring surface anatomical features in medical images.

Medical imaging technology, such as magnetic resonance imaging (MM), computerized axial tomography (CT or CAT) scans, and the like, provides detailed three-dimensional (3D) views of a patient's internal anatomical structures (e.g., tissues and/or organs). The images may be captured as a set of two-dimensional (2D) "slices" through the patient's body, from which a 3D representation of the imaged portion of the patient's body can be generated. The 3D representation, referred to herein as a "medical image," consists of an arrangement of three-dimensional image elements (referred to as "voxels") with assigned intensity values based on the imaging process.

In addition to diagnosing a condition in an individual patient, medical images may also be useful in medical research and/or training. For instance, medical knowledge can be advanced by analyzing medical images of a number of patients with a known condition in order to identify features that may be relevant for diagnosis of future patients. For such reasons, it may be desirable to share medical images with persons other than the patient and the patient's healthcare provider(s).

However, sharing of medical images with third parties may unacceptably compromise patient privacy. For instance, a medical image may provide sufficiently detailed information about surface anatomical features of the patient (e.g., facial features such as shape of eyes, nose, mouth, ears, etc.) to allow the patient's identity to be determined (e.g., using the facial recognition ability of a person or automated system). Consequently, sharing such images could be a violation of privacy protection laws or regulations. To enable sharing of medical images without compromising patient privacy, it would be desirable to modify a medical image in a way that obscures surface anatomical features (so that the patient cannot be recognized) without altering the medically-useful information (e.g., portions of the medical image representing internal anatomical structures). Such modifications are referred to as "de-identification" of an image.

Several de-identification techniques are currently in use. One such technique, used in the context of brain MRI, is referred to as "skull stripping." This technique entails using a computer algorithm to identify and remove voxels that correspond to non-brain tissue from a medical image of a patient's brain, based on assumptions or models about the likely location of brain tissue in a medical image. In practice, skull stripping can be vulnerable to imaging artifacts, and voxels corresponding to brain tissue may be inadvertently removed. Manual intervention is generally required to prevent or correct such errors. In addition, non-brain tissue may be useful for some studies, and removing non-brain areas from the medical image can limit the usefulness of the image for research.

Another conventional de-identification technique is referred to as "defacing." A facial probability map is created, defining the likelihood that voxels in a particular region would correspond to a patient's face. A rigid-body image registration algorithm is used to align a medical image to the facial probability map, allowing removal of voxels with a nonzero probability of corresponding to the patient's face. The defaced image hides the patient's facial features while preserving internal brain voxels. This technique requires a reliable facial probability map, and generating such maps has proven difficult. It is generally necessary to create the map manually or rely on an average across a number of images. Facial maps are also generally non-transferable across imaging modalities or datasets with high morphological variability. Further, defacing algorithms typically result in removal of some internal structures (such as nasal cavities), which may limit the usefulness of the image for research.

In general, existing techniques for de-identifying medical images are computationally intensive and/or require significant manual intervention. In addition, these techniques may be susceptible to error, as they rely on image registration techniques that may not be applicable in a particular case. Improved de-identification techniques for medical images would therefore be desirable.

SUMMARY

Certain embodiments of the present invention relate to systems and methods for de-identification of medical images. The systems and methods described herein can be applied to medical images acquired using various techniques such as MRI, CT, and the like. In some embodiments, a 3D medical image is analyzed to generate an image mask that partitions the image into a foreground region (a region containing voxels where anatomical features of the patient may be present) and a background region (a region containing voxels outside the patient's body). From the image mask, a "skin surface" can be reconstructed based on the boundary between the foreground region and the background region. Once generated, the image mask can be modified, e.g., by moving a randomly-selected subset of the voxels from the foreground region to the background region so that the shape of the skin surface is altered, thus obscuring patient-identifying features. After modifying the image mask, the original medical image can be modified by setting the intensity value of all voxels in the background region to a background value (e.g., zero intensity) while preserving the intensity value of all voxels in the foreground region. These processing operations can be fully automated with low computational complexity, making them suitable for large-scale applications.

In some embodiments, the image mask can be approximated by identifying as the background region the largest region of contiguous voxels having background intensity levels (e.g., low intensity) and identifying all other voxels as the foreground region. This initial approximation can be refined using morphological corrections and/or a supervoxel analysis. The image mask can be defined such that the reconstructed skin surface conforms fairly closely to the patient's surface anatomical features.

In some embodiments, modification of the image mask can include randomly selecting a set of seed points on the reconstructed skin surface and applying a kernel to select voxels around the seed point to be moved from the foreground region to the background region. Additional smoothing and other modifications can be applied to further obfuscate the original shape of the skin surface.

De-identification procedures as described herein can result in medical images in which surface anatomical features are obscured sufficiently that the patient is not recognizable while voxels corresponding to internal anatomy are preserved. At the same time, the medical image retains enough information to allow reconstruction of a non-patient-identifying skin surface. Such de-identified images can be used in research studies, presentations, publications, and other contexts where it is desirable to avoid revealing a patient's identity.

The following detailed description, together with the accompanying drawings, will provide a better understanding of the nature and advantages of the claimed invention.

BRIEF DESCRIPTION OF THE DRAWINGS

FIG. 1A shows a two-dimensional image of an axial (or transverse) slice of a patient's brain, and FIG. 1B shows front, side, and top views of a 3D rendering of a patient's head as reconstructed from a medical image.

FIG. 2 is a flow diagram of a process for de-identification of medical images according to an embodiment of the present invention.

FIGS. 5A-5E illustrate image-processing stages in the process of FIG. 4. FIG. 5A illustrates an example of applying spatial normalization to an image. FIG. 5B shows an example of an axial slice of 3D image data that has been segmented into regions. FIG. 5C shows an axial slice of an example result of applying connectivity analysis to the 3D image data. FIG. 5D shows an example of a first approximate image mask obtained for the axial slice of FIG. 5C.

FIG. 5E shows a result of morphological correction applied to the approximate image mask of FIG. 5D.

FIG. 8A is an axial view, FIG. 8B is a coronal view, and FIG. 8C is a sagittal view.

FIG. 9A shows a super-voxel map for an axial slice of 3D image data. FIG. 9B shows the super-voxel map of FIG. 9A after separation of disconnected parts of the super-voxels.

FIG. 11A shows a representative axial slice of an approximate image mask. FIG. 11B shows a 3D view of a reconstructed skin surface 1110 from an approximate image mask. FIGS. 11C and 11D show views corresponding to FIGS. 11A and 11B, respectively, but using a refined image mask.

FIGS. 15A-15D and 16A-16D illustrate examples of de-identification of images according to an embodiment of the present invention. FIGS. 15A-15D show 3D views of skin surface reconstructions from four different medical images. FIGS. 16A-16D show skin-surface reconstructions generated from the same MRI images as FIGS. 15A-15D, respectively, after applying a de-identification process according to an embodiment of the present invention.

DETAILED DESCRIPTION

Certain embodiments of the present invention relate to systems and methods for de-identification of medical images. As used herein, a "medical image" refers to a three-dimensional (3D) image that reveals features of the internal anatomy of a patient (where the term "patient" refers generally to any person subjected to medical imaging). Medical images may be generated using a variety of imaging technologies, including such well-known technologies as magnetic resonance imaging (MRI), computerized axial tomography (CT or CAT) scans, or the like. (MRI images are used herein for purposes of illustration.)

Due to the nature of medical imaging technologies, medical images may also include information about surface anatomical features of the patient. As used herein, a "surface anatomical feature" refers to a feature of the patient's anatomy that is externally visible. Some surface anatomical features may be usable to determine the patient's identity. Examples include facial features such as eyes, nose, mouth, ears, chin, etc., although the invention is not limited to facial features and may be applied to medical images of any portion of a patient's body.

Figure 1A:
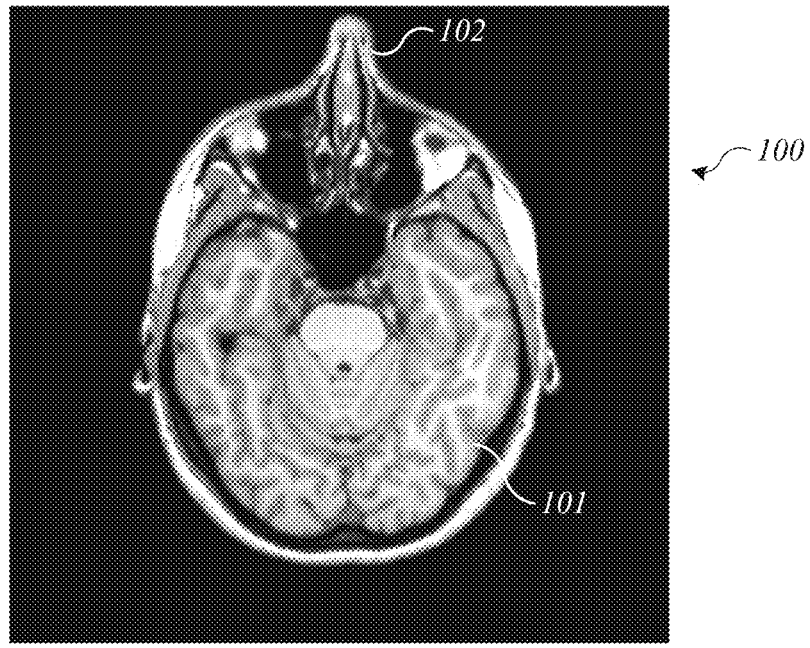
FIGS. 1A and 1B illustrate the potential to reconstruct patient-identifying surface anatomical features from a 3D medical image.
Figure 1B:
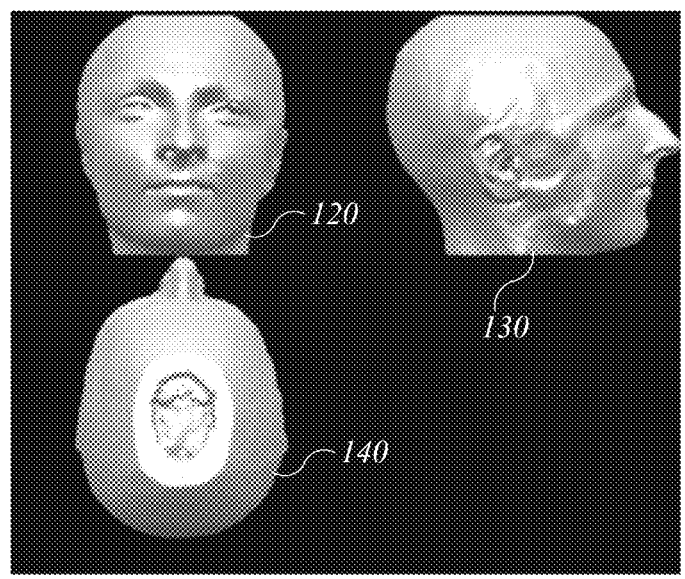

FIGS. 1A and 1B illustrate the potential to reconstruct patient-identifying surface anatomical features from a medical image. Shown in FIG. 1A is a two-dimensional image 100 of an axial slice of a patient's brain. Images such as image 100 are routinely obtained from patients using MRI scanners or the like. (The particular details of obtaining a medical image are not relevant to understanding the present disclosure, and a description of imaging technologies and processes is omitted.) A number of medical imaging processes involve obtaining a set of 2D images similar to image 100, from which a three-dimensional model of an anatomical structure of interest (e.g., the patient's brain or other organs) can be constructed.

As can be seen in FIG. 1A, image 100 reveals internal anatomical structures such as brain 101. Image 100 can also reveal surface anatomical features of the patient. For instance, a cross-section of the patient's nose 102 can be seen. Consequently, using 3D data obtained during medical imaging, a reconstructed image (or rendering) of the patient's surface anatomy can be obtained. FIG. 1B shows coronal (120), sagittal (130), and axial (140) views of a 3D rendering of a patient's head as reconstructed from a 3D MRI image. Distinctive facial features, such as eyes, nose, mouth, ears, and chin are visible. In principle, it would be possible for someone (either a person viewing the rendering or a computer-based image-analysis system) to identify the patient whose head was imaged. Thus, 3D medical imaging has the potential to compromise patient privacy.

Embodiments of the present invention provide systems and methods that can de-identify medical images by modifying the image data to obscure surface anatomical features (such as the facial features in FIG. 1B), without compromising the portions of the image data pertaining to internal anatomical structures. In some embodiments, the de-identification process can be based entirely on the medical image being de-identified, plus some general assumptions about human anatomy and the characteristics of the medical imaging technology; no templates or models are required. In some embodiments, a de-identification process can be fully automated, computationally efficient, and easily transferable across imaging modalities.

De-Identification Process Overview

FIG. 2 is a flow diagram of a process 200 for de-identification of medical images according to an embodiment of the present invention. Process 200 can be implemented in a computer system, e.g., by writing appropriate program code to be executed by a processor. In some embodiments, process 200 can be fully automated so that no human intervention is required.

Process 200 can begin with obtaining a set of medical images of a patient at block 202. In some embodiments, block 202 can include imaging the patient and recording data; in other embodiments, previously recorded image data may be obtained from a computer-readable storage medium. The particular imaging technology can be chosen as desired and may be, e.g., MRI or CT or the like. For purposes of description, it is assumed that the imaging technology produces a medical image that can be represented as a three-dimensional (3D) grid of voxels, where each voxel has an intensity value within a finite range from a minimum value to a maximum value. For purposes of illustration, the intensity scale is assumed to have a minimum value of 0 and a maximum value of 255. It is also assumed that voxels where no tissue is present would have minimum intensity; where tissue is present, intensity is assumed to vary depending on the type and density of tissue and the particular imaging modality. Those skilled in the art with access to the present disclosure will understand that other intensity scales can be substituted. It should also be understood that a 3D medical image can be produced in a scanning operation that generates images of a set of 2D slices of a patient's anatomy, from which the 3D representation can be constructed.

At block 204, an image mask and a corresponding skin surface are generated from the medical image. The image mask can indicate a classification of each voxel of the medical image as belonging to either a "foreground" region or a "background" region. The foreground/background classification can be mutually exclusive and jointly exhaustive. In some embodiments, the image mask can be represented using a bitmask with one bit per voxel; a value of 1 (0) can indicate a foreground (background) voxel. Other representations can be used.

Figures 3A, 3B:
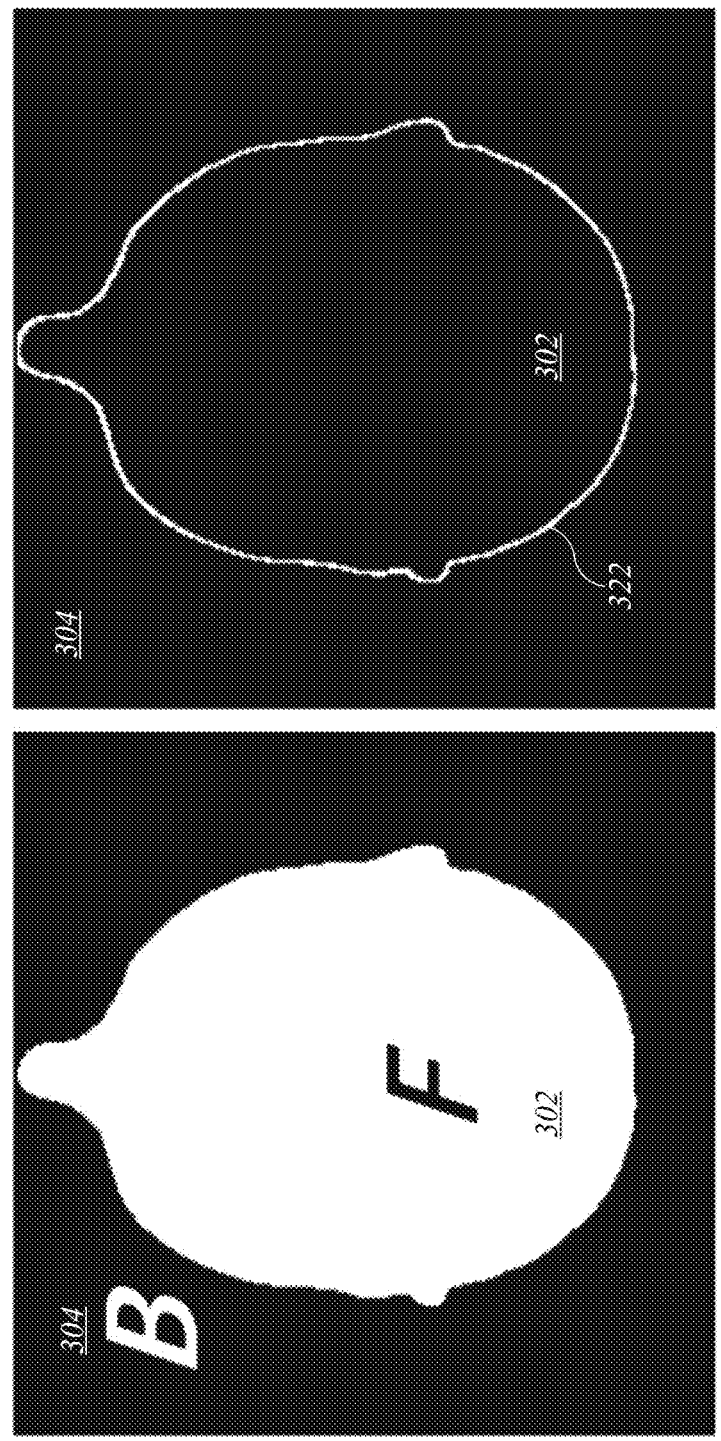
FIG. 3A shows an axial slice view of an image mask according to an embodiment of the present invention.
FIG. 3B shows a boundary between foreground and background regions for the image mask of FIG. 3A.

The classification of foreground and background regions is intended to distinguish voxels corresponding to locations in or on the patient's body (referred to as "foreground") from voxels corresponding to locations outside the patient's body (referred to as "background"). By way of illustration, FIG. 3A shows an axial slice view of an image mask 300 according to an embodiment of the present invention. Foreground region 302 (also labeled "F") is color-coded in white, and background region 304 (also labeled "B") is color-coded in black. As shown in FIG. 3B, the boundary between foreground region 302 and background region 304 can be defined as a "skin surface" 322. In some embodiments, the image mask for a particular medical image is generated such that skin surface 322 closely conforms to the actual contours of the patient's body. (It should be noted that "skin surface" is used herein to refer to the outer boundary of a foreground region such as region 302 and does not necessarily correspond to "skin" as an anatomical structure.)

In some embodiments, generation of the image mask and skin surface can proceed in two stages. For instance, at block 206, an approximate image mask and skin surface can be generated by identifying contiguous regions where the voxels have similar intensity, then identifying as a background region the largest such region having low (background-level) intensity. At block 208, the approximate image mask and skin surface can be refined using a super-voxel analysis. Examples of specific processes that can be implemented at blocks 206 and 208 are described below.

At block 210, the boundary between foreground and background regions of the image mask is modified, e.g., by moving a randomly-selected subset of voxels from the surface of foreground region 302 to background region 304. The voxels to be moved are selected in a manner that modifies the shape of the boundary between foreground region 302 and background region 304, so that a skin-surface reconstruction based on the modified image mask is no longer patient-identifying. Examples of specific processes are described below.

At block 212, the original image data is modified based on the image mask. For example, intensity value for all voxels in (modified) background region 304 can be set to a nominal background intensity value (e.g., 0) while the original intensity values for all voxels in (modified) foreground region 302 are preserved. As will become apparent, the result of process 200 is a de-identified medical image, in which voxels corresponding to internal anatomical structures are unmodified while the shape of the skin surface is modified such that the patient is not identifiable from a reconstruction of the skin surface. Such de-identified images can be shared and/or published without compromising patient privacy.

Example implementations of specific processing stages of image de-identification process 200 will now be described.

Generating an Approximate Image Mask

Figure 4:
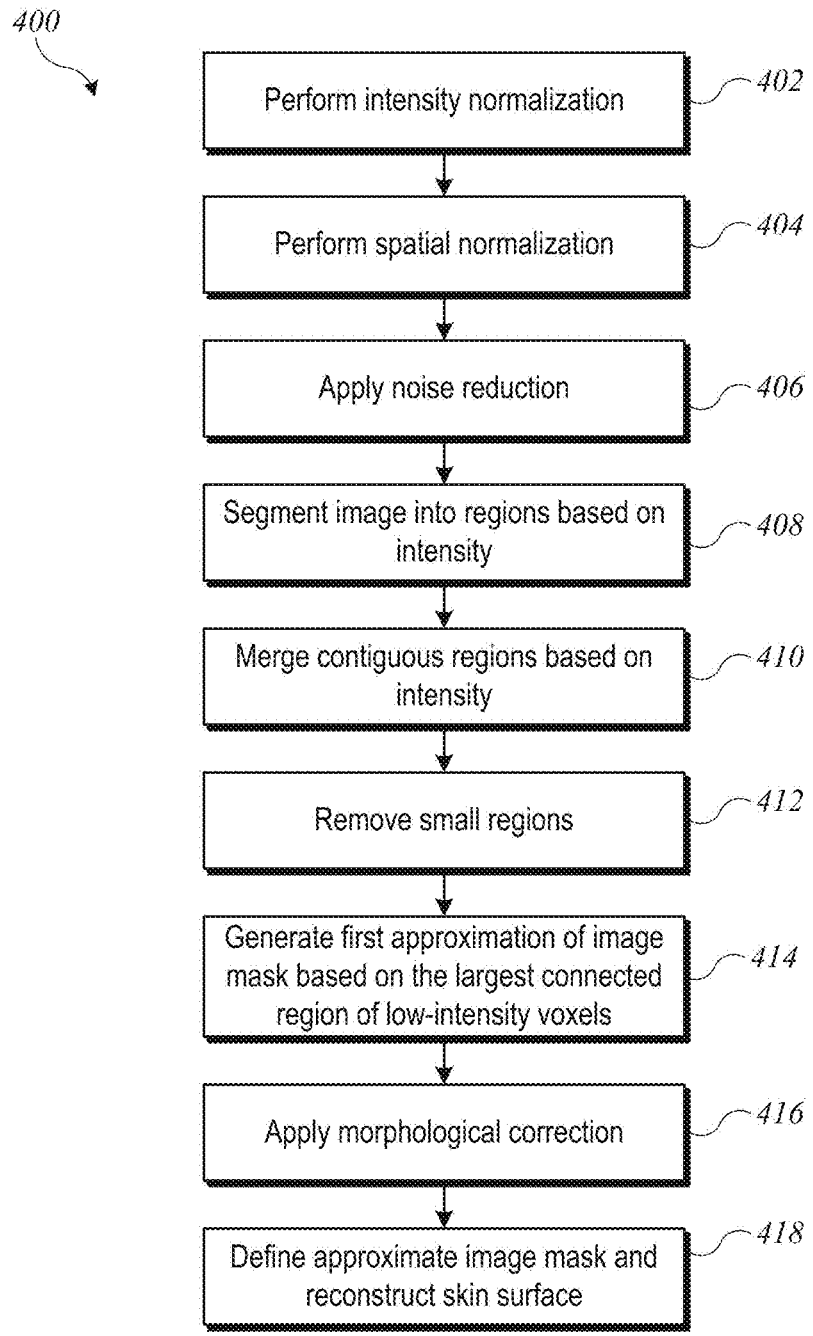
FIG. 4 shows a flow diagram of a process for generating an approximate image mask from medical image data according to an embodiment of the present invention.

FIG. 4 shows a flow diagram of a process 400 for generating an approximate image mask and a skin surface from medical image data according to an embodiment of the present invention. Process 400 can be implemented, e.g., at block 206 of process 200 of FIG. 2. Like other blocks of process 200, process 400 can be implemented in a computer system, e.g., by writing appropriate program code to be executed by a processor. In some embodiments, process 400 can be fully automated so that no human intervention is required.

Process 400 assumes that the background portion of a medical image (voxels not corresponding to part of the patient's body) includes the largest contiguous (or connected) region of dark (low-intensity/low-signal) voxels, while the foreground portion (voxels corresponding to some part of the patient's body) has variable intensity that is generally higher than the background intensity. Accordingly, process 400 can include specific operations to identify the largest contiguous region of low-intensity voxels. In some embodiments, process 400 produces an approximate image mask and skin surface that can be used directly for de-identification or refined through further processing prior to use for de-identification.

To facilitate identification of a background region, process 400 can begin with image normalization. For instance, at block 402, intensity normalization can be applied. One normalization procedure includes calculating a cumulative intensity histogram of the input image, defining a lower intensity threshold (T1) such that 2% of the voxels have intensity below T1, and defining an upper intensity threshold (T2) such that 98% of the voxels have intensity below T2. The intensity scale of the input image (e.g., 0 to 255) can be linearly stretched by mapping T1 to the minimum intensity (e.g., 0) and T2 to the maximum intensity (e.g., 255) and rescaling values between T1 and T2 according to a linear mapping. Voxels with intensity below T1 can be assigned the minimum intensity, and voxels with intensity above T2 can be assigned the maximum intensity. In some embodiments, the normalized image data is saved separately from the original image data.

At block 404, spatial normalization can be applied to the intensity-normalized image produced at block 402. For example, the center of gravity (COG) of the image can be computed using existing techniques. Using the computed COG position, the image can be spatially normalized (shifted and/or scaled) to a pre-defined standard space. FIG. 5A shows an example of applying spatial normalization to an input image 502 (shown in sagittal slices). As shown, input image 502 is misaligned relative to a standard space 504 (also shown in sagittal slices). Block 404 can shift image 502 in space to better align with standard space 504.

At block 406, noise reduction can be applied to the normalized image. For example, an iterative Gaussian filter can be used. Such filters are well-known in the art. Other noise-reduction filters may also be used in addition to or instead of the iterative Gaussian filter.

At block 408, the noise-reduced image is segmented into labeled regions based on the intensity value of each voxel, with voxels of similar intensity being assigned the same label (or region). In some embodiments, a series of intensity thresholds is defined, and each voxel is assigned an intensity label based on the intensity threshold. In one example where intensity values are integers ranging from 0 to 255, ten intensity thresholds are defined (e.g., at 25, 50, 75, 100, etc.); label 1 (or region 1) is assigned to all voxels with intensity up to 25, label 2 to all voxels with intensity from 26 to 50, etc. FIG. 5B shows an example of an axial slice of 3D image data that has been segmented in this manner; an arbitrary color-coding scheme has been applied to indicate the different labels.

At block 410, contiguous regions having the same intensity label can be merged.

Connectivity analysis to identify contiguous regions with the same intensity label can be performed in 3D space. FIG. 5C shows an example result of applying connectivity analysis to a 3D image that includes the axial slice of FIG. 5B; again, an arbitrary color-coding scheme has been applied to indicate different regions. As can be seen, this reduces the number of regions to be considered in subsequent blocks of process 400.

At block 412, a volume (e.g., number of voxels) and average intensity can be computed for each region resulting from block 410. Small regions (e.g., fewer than 5000 voxels) can be ignored in subsequent blocks of process 400, as the immediate aim is to identify a large contiguous region of voxels having low background-like (e.g., low) intensity.

At block 414, a first approximation of an image mask is generated by identifying the largest region having low average intensity as a background region and identifying all other regions as a foreground region. In one example implementation, an intensity threshold (T3) is determined such that 10% of the regions remaining after block 412 have average intensity below T3. Regions with intensity greater than T3 are ignored, and the largest remaining region is identified as the first approximation of the background region. FIG. 5D shows an example of a first approximate image mask obtained for the axial slice of FIG. 5C. Green region 540 is the background region and black regions 542, 544 are foreground regions. As can be seen, the first approximation may be inexact: some areas 544 that are identified as part of the foreground region are, based on general properties of human anatomy, more likely to be part of the background.

To improve this first approximation, at block 416, a morphological correction can be applied to the first approximate image mask identified at block 414 to produce a second approximate image mask. Morphological correction can remove small bumps and holes from the foreground region, thereby producing a second approximate image mask. The morphological correction can include an opening operation (erosion followed by dilation) followed by a closing operation (dilation followed by erosion); these are well known operations in digital image processing, and a detailed description is omitted. FIG. 5E shows a result of morphological correction applied to the first approximate image mask of FIG. 5D. Some areas 544 of FIG. 5D have disappeared entirely, and others have been reduced in size.

Figure 6:
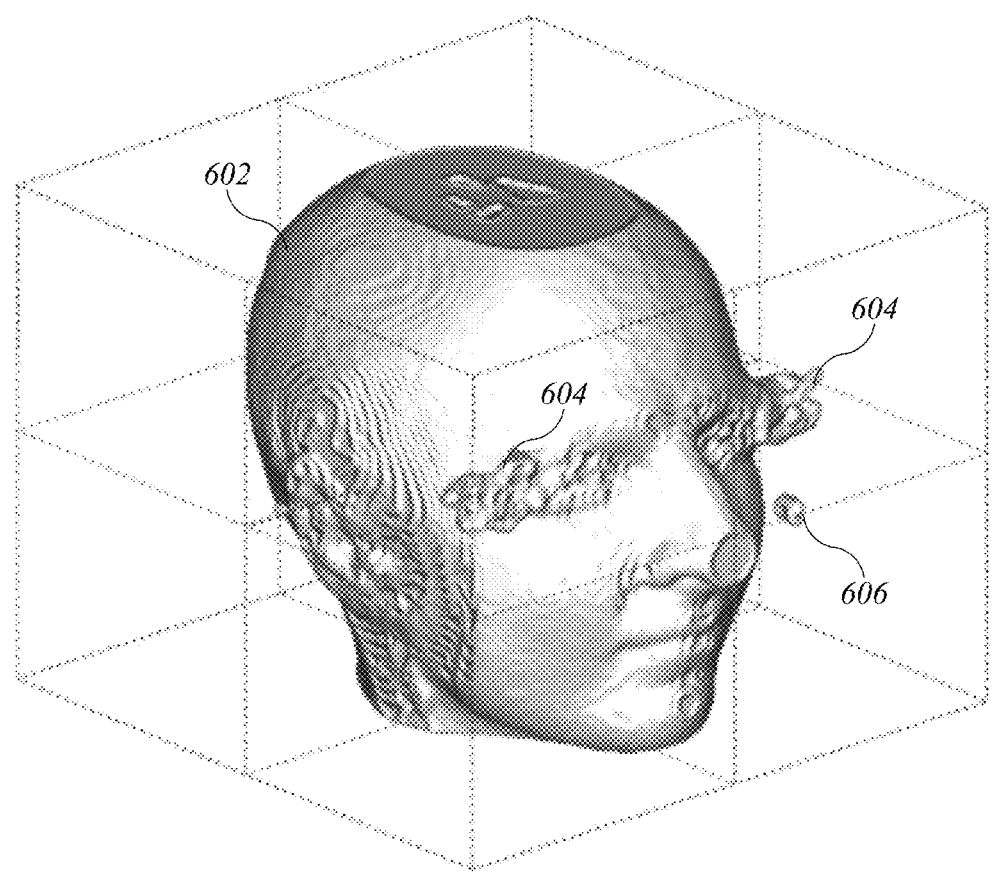
FIG. 6 shows a 3D view of a skin surface reconstructed from an approximate image mask generated using the process of FIG. 4 according to an embodiment of the present invention.

At block 418, an approximate skin surface can be reconstructed from the second approximate image mask, e.g., by generating a geometric surface that conforms to the boundary between the background region and the foreground region. FIG. 6 shows a 3D view of a skin surface 602 reconstructed from an approximate image mask generated according to an embodiment of the present invention.

Refining the Image Mask

As can be seen in FIG. 6, a reconstructed skin surface produced using process 400 may deviate from expected human anatomy. For instance, portions of the skin surface near the eyes (areas 604) may deviate from human features, and there may be extraneous voxels (e.g., area 606) that are not part of the patient's body. Accordingly, in some embodiments of the invention, an approximate image mask obtained using voxel-level connectivity analysis (e.g., process 400) can be refined using additional processing.

Figure 7:
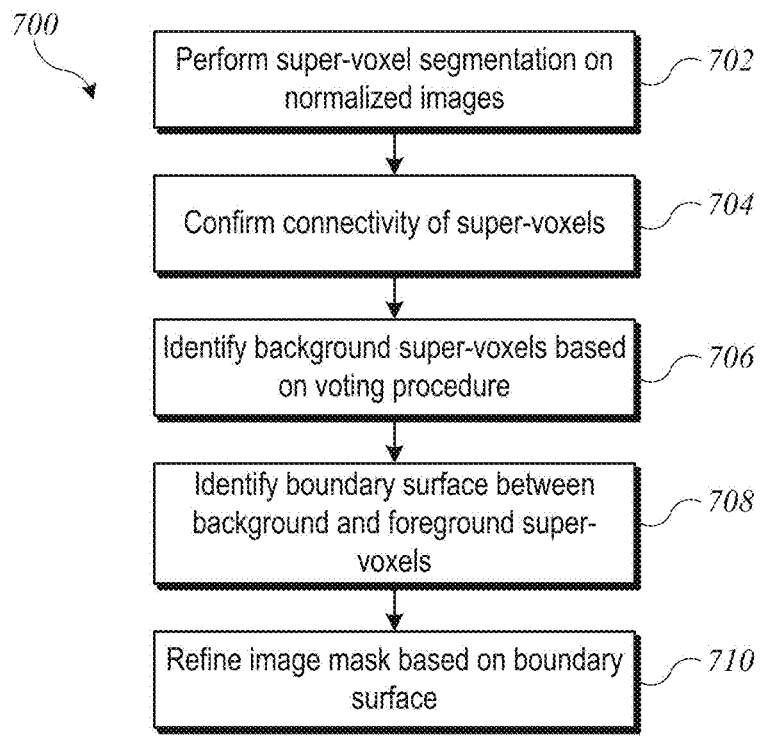
FIG. 7 shows a flow diagram of a process for refining an approximate image mask obtained from medical image data according to an embodiment of the present invention.

FIG. 7 shows a flow diagram of a process 700 for refining an approximate image mask obtained from medical image data according to an embodiment of the present invention. Process 700 can be implemented, e.g., at block 208 of process 200 of FIG. 2. Like other blocks of process 200, process 700 can be implemented in a computer system, e.g., by writing appropriate program code to be executed by a processor. In some embodiments, process 700 can be fully automated so that no human intervention is required. Process 700 makes use of a "super-voxel" procedure that can be applied to combine image voxels into perceived meaningful regions, replacing the regular structure of a voxel grid with super-voxels of varying size. Compared to voxel-wise image segmentation, super-voxel segmentation provides improved boundary adherence, which makes it useful for refining an approximate image mask generated at block 206 of process 200 (e.g., using process 400). The boundary voxels identified for the approximate skin surface can be used to select appropriate super-voxels to use in the further refinement.

Figure 8C:
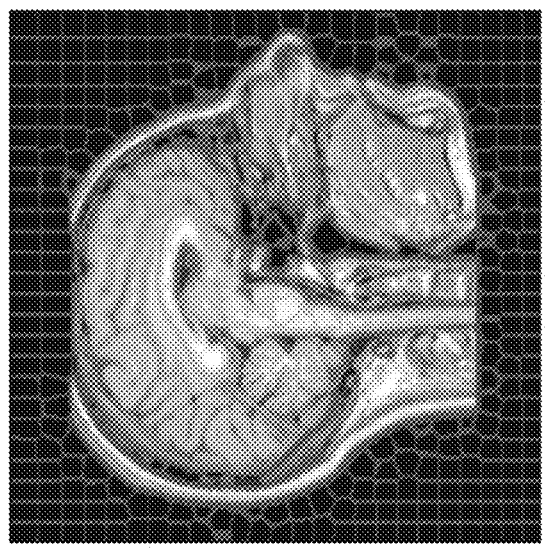
FIGS. 8A-8C show three cross-section views of a 3D medical image segmented into a super-voxel image.
Figure 8B:
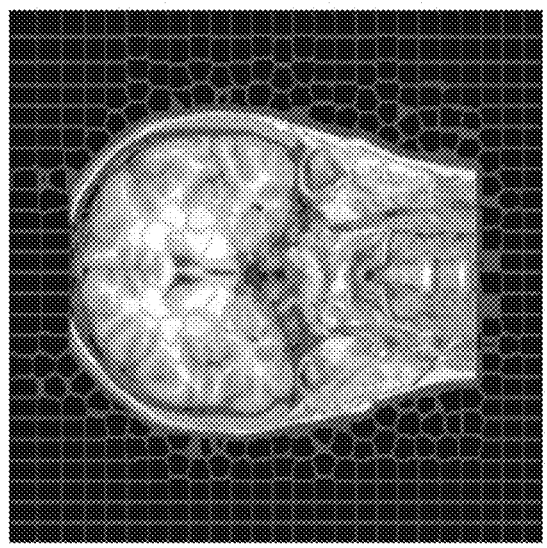
Figure 8A:
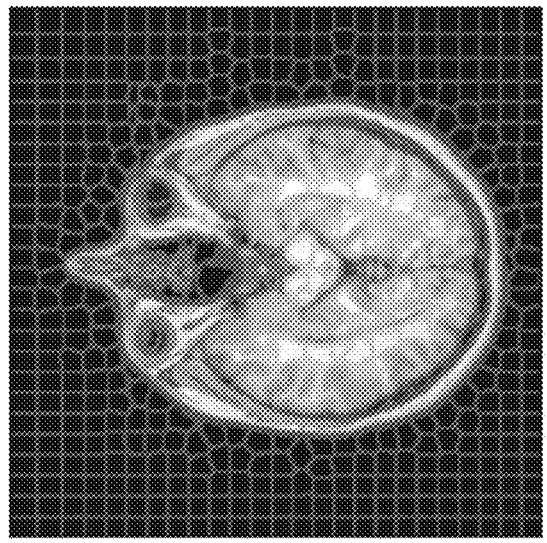

At block 702, medical image data (e.g., data resulting from block 404 of process 400) can be segmented into a super-voxel image, e.g., using the SLIC algorithm described in R. Achanta et al. *Slic superpixels* (No. EPFL-REPORT- 149300) (2010); R. Achanta et al., "SLIC superpixels compared to state-of-the-art superpixel methods," *IEEE Transactions on Pattern Analysis and Machine intelligence,* 34(11), 2274-2282 (2012); and K. S. Kim et al., "Improved simple linear iterative clustering superpixels," *IEEE 17th International Symposium on Consumer Electronics (ISCE)* (2013). In some embodiments, the approximate image mask generated at block 206 of process 200 can be used to reduce the region subjected to super-voxel segmentation to those regions that are near the foreground/background boundary, thereby reducing the computational burden. FIGS. 8A-8C show three cross-section views of a 3D medical image segmented into a super-voxel image: FIG. 8A is an axial view, FIG. 8B is a coronal view, and FIG. 8C is a sagittal view. The green lines indicate the super-voxels. As can be seen near the boundaries of the foreground region, the super-voxels do not conform to a regular grid.

Figure 9B:
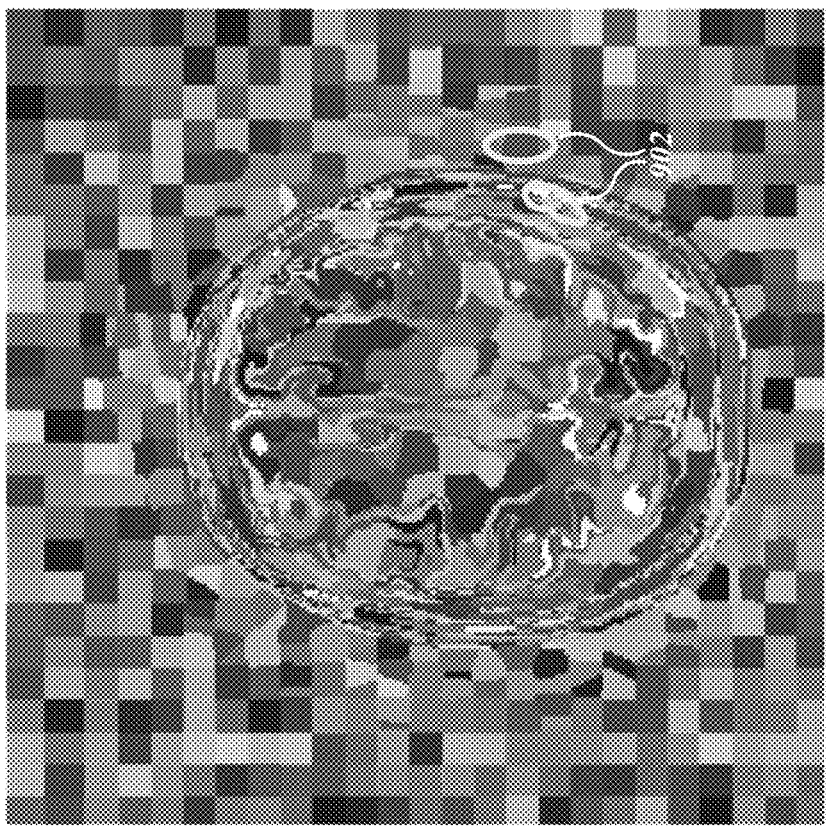
FIGS. 9A-9B illustrate separating disconnected parts of a super-voxel according to an embodiment of the present invention.
Figure 9A:
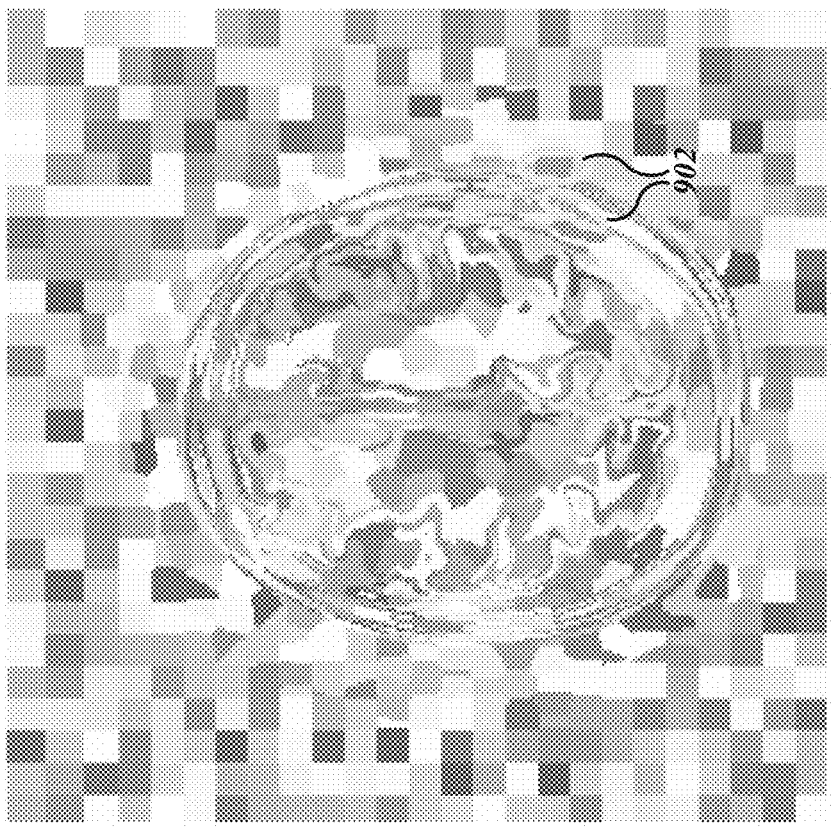

The SLIC algorithm does not guarantee connectivity of the super-voxels. For instance, disconnected image regions may be clustered into the same super-voxel. As a result, some portions of a super-voxel may be in the foreground region while other portions are in the background region. To reduce error in identifying the boundary between foreground and background regions, connected component analysis can be performed at block 704 to confirm connectivity of the super-voxels. Disconnected parts of a super-voxel can be separated into different super-voxels. FIGS. 9A-9B illustrate an example case where connected component analysis results in separating a super-voxel. Shown in FIG. 9A is a super-voxel map for a representative axial slice through the 3D image data. An arbitrary color-coding scheme is used to distinguish different super-voxels. Yellow rings 902 have been added to mark two disconnected parts of a single super-voxel (both parts have the same light purple color). Connected component analysis can detect that the parts are disconnected. FIG. 9B shows the super-voxel map of FIG. 9A after separation of disconnected parts of the super-voxels. Yellow rings 902 (in the same location as in FIG. 9A) now mark two different super-voxels (teal and dark purple).

Figure 10:
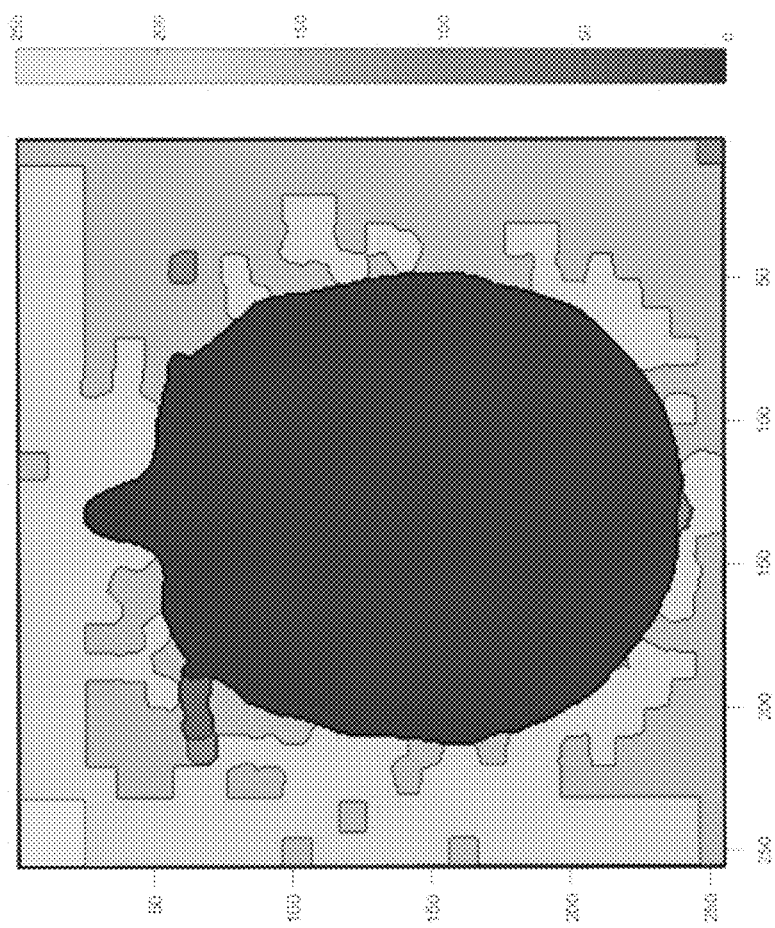
FIG. 10 shows an example of a foreground and background weight map for a representative axial image slice obtained from super-voxels according to an embodiment of the present invention.

At block 706, background super-voxels can be identified by applying a voting procedure to the modified super-voxel image from block 704. In one implementation, the voting procedure is based on counting the number of background voxels in each super-voxel. Based on the counts, a foreground and background weight map can be produced. FIG. 10 shows an example of a foreground and background weight map for a representative axial image slice. The map is color-coded as shown at the right, with purple indicating super-voxels with the lowest number of background voxels and yellow indicating super-voxels with the highest number of background voxels. A threshold can be chosen such that any super-voxel with more than the threshold number of background voxels is labeled as a background super-voxel while all other super-voxels are labeled as foreground super-voxels. In one embodiment, a threshold of 100 voxels is chosen.

At block 708, a boundary surface between the background and foreground super-voxels can be identified. At block 710, the image mask can be refined based on the boundary surface identified at block 708. For instance, all voxels inside the boundary surface can be assigned to the foreground region in the image mask, while all voxels outside the boundary surface are assigned to the background region.

Figure 11B:
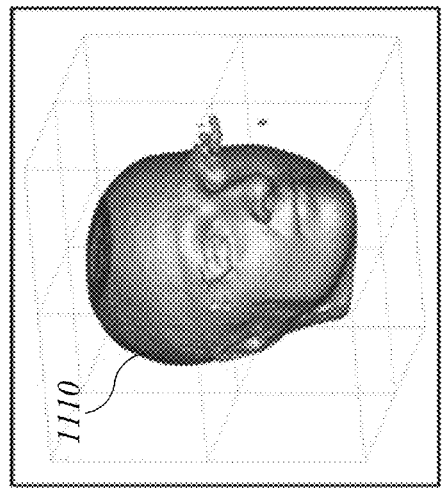
FIGS. 11A-11D illustrate an example of an effect of applying the process of FIG. 7 according to an embodiment of the present invention.
Figure 11D:
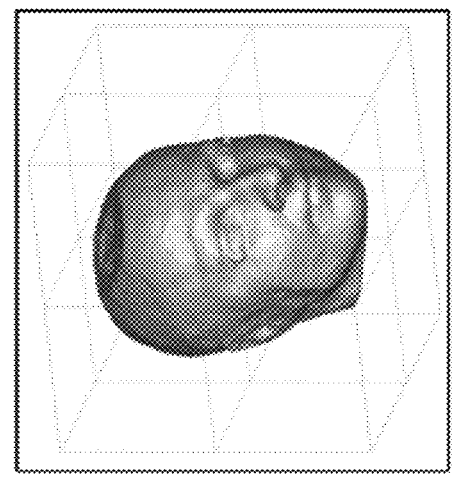
Figure 11A:
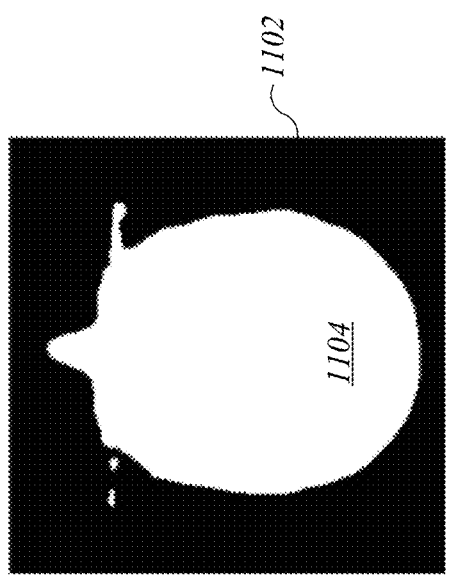
Figure 11C:
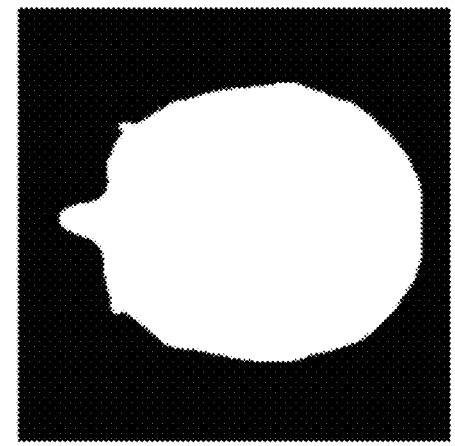

In some embodiments, process 700 can refine the approximate image mask obtained from process 400, so that the reconstructed skin surface more closely tracks the patient's anatomy. FIGS. 11A-11D illustrate an example of the effect of such refining. FIG. 11A shows a representative axial slice of an approximate image mask generated using an implementation of process 400. The approximate image mask has a background region (black region 1102) and foreground region (white region 1104). FIG. 11B shows a 3D view of a reconstructed skin surface 1110 from an approximate image mask generated using an implementation of process 400. As can be seen, some voxels are misclassified. FIGS. 11C and 11D show views corresponding to FIGS. 11A and 11B, respectively, except that the approximate image mask has been refined using an implementation of process 700. Misclassification of voxels is visibly reduced.

Modifying the Skin Surface

A result of processes 400 and 700 (or just process 400) is an image mask from which a skin surface can be reconstructed. The reconstructed skin surface may reveal identifying features of the patient. Such identifying features can be effectively removed by modifying the image mask, e.g., by modifying the boundary between foreground and background regions of the image mask at block 210 of process 200 of FIG. 2.

In some embodiments, modifying the image mask can include reassigning some voxels from the foreground region to the background region such that the shape of the boundary between foreground and background regions is altered. In other embodiments, modifying the image mask can also include reassigning some voxels from the background region to the foreground region, although adding voxels to the foreground region may entail adding what amounts to noise to the original image (so that the added foreground voxels look like they belong to the patient's body). Such added noise may not be desirable in some contexts, such as where researchers could be misled by the added information.

Figure 12:
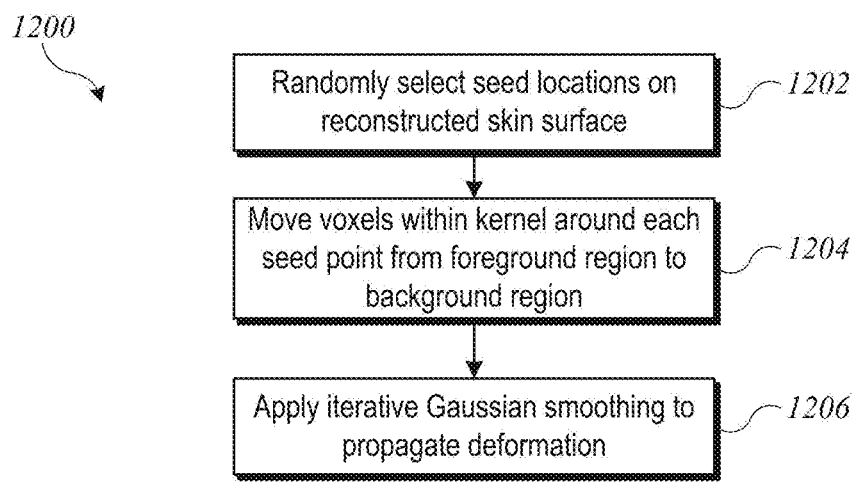
FIG. 12 shows a flow diagram of a process for modifying an image mask generated from medical image data according to an embodiment of the present invention.

FIG. 12 shows a flow diagram of a process 1200 for modifying an image mask generated from medical image data according to an embodiment of the present invention. Process 1200 can be implemented, e.g., at block 210 of process 200 of FIG. 2. Like other blocks of process 200, process 1200 can be implemented in a computer system, e.g., by writing appropriate program code to be executed by a processor. In some embodiments, process 1200 can be fully automated so that no human intervention is required.

Figure 13:
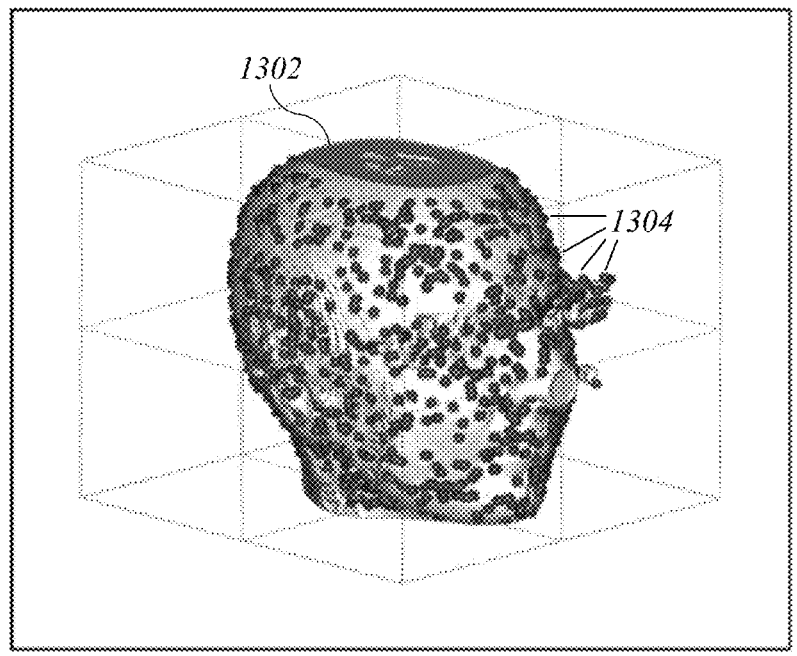
FIG. 13 shows a 3D view of a reconstructed skin surface on which seed locations are randomly distributed according to an embodiment of the present invention.

At block 1202, a set of "seed" locations on a skin surface can be selected. In embodiments described herein, the skin surface is reconstructed from an image mask, e.g., in connection with process 400 or process 700 described above. In some embodiments, the skin surface can be reconstructed as a triangle mesh or other polygon mesh using conventional techniques for representing object geometry. For each vertex of the mesh, a random number can be generated and used to determine whether to select that vertex as a seed location. In one example, the random numbers are in the range from 0 to 100 (with uniform distribution), and a vertex is selected as a seed location if the random number is 99 or higher, so that each vertex has approximately a 1% probability of being selected as a seed location. Conventional or other algorithms for generating a random or pseudorandom sequence of numbers may be used, and the probability of selecting a vertex as a seed location can be modified. Other techniques for randomly selecting seed locations on a surface may be used, and the density of seed locations can be varied, e.g., by increasing or decreasing the probability of selecting a vertex as a seed location. FIG. 13 shows a 3D view of a reconstructed skin surface 1302 on which seed locations (red dots 1304) are randomly distributed according to an embodiment of the present invention.

Figure 14:
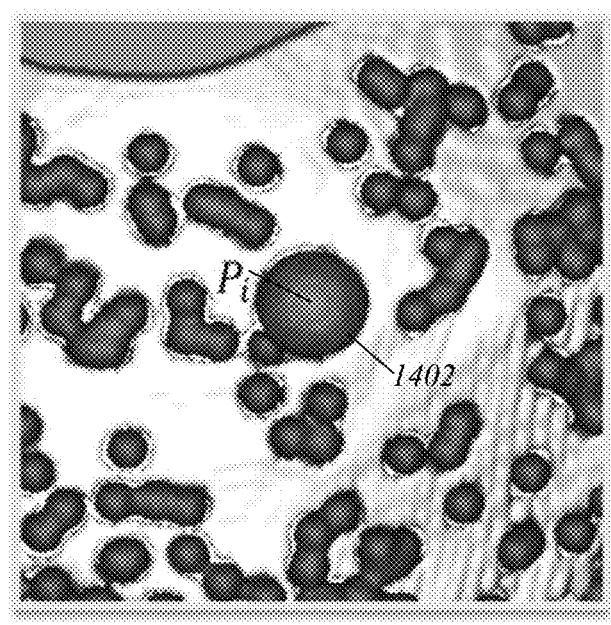
FIG. 14 shows a spherical kernel around a seed point $P_i$ according to an embodiment of the present invention.

At block 1204, a kernel can be used to "corrode" the foreground region mask around the seed locations. The kernel can be an invariant shape that is iteratively applied at each seed location, and any voxels within the kernel that had been assigned to the foreground region can be reassigned to the background region. By way of illustration, FIG. 14 shows a spherical kernel 1402 (purple) around a seed location $P_i$ according to an embodiment of the present invention. Any foreground voxels within kernel 1402 are reassigned to the background region. In various embodiments, the size and shape of the kernel can be modified. The kernel can be selected empirically. A larger kernel results in the removal of more voxels from the foreground region and may also result in removing voxels corresponding to internal anatomical structure. Accordingly, the kernel size can be chosen to be large enough to result in obscuring the patient's identity but small enough to avoid loss of medically useful information.

While kernel-based corrosion of the image mask at block 1204 can alter the shape of the skin surface enough to obscure identifying features, the regularity of the kernel size and shape may make it possible to recover the original skin surface from a de-identified image. To prevent such recovery, at block 1206, iterative Gaussian smoothing can be applied to propagate the deformation on the surface. In one embodiment, n=3 iterative Gaussian smoothing is performed. A relatively smooth Gaussian kernel can be used to preserve more image voxels. The Gaussian smoothing has the effect of blurring details of the skin surface, as well as preventing recovery of the original skin surface. Other techniques, such as randomly varying the kernel applied at different seed points, may also be used to prevent recovery of the original skin surface.

Referring again to FIG. 2, at block 212, after the image mask has been modified (e.g., using process 1200), a de-identified image can be produced by modifying the original image data based on the modified image mask. In some embodiments, modifying the original image data to produce the final de-identified image includes setting the intensity value to zero for all voxels that are in the background region defined by the modified image mask. Applying the same intensity value to all voxels in the background region renders voxels that were originally background indistinguishable from voxels that were reassigned to the background region during modification of the image mask. All voxels within the foreground region of the image mask can retain their original intensity values.

It should be noted that, in embodiments where spatial normalization was performed as part of generating the image mask (e.g., at block 404 of process 400 of FIG. 4), block 212 can include reversing the spatial normalization to improve registration between the modified image mask and the original image data prior to modifying the original image data. For instance, if spatial normalization at block 404 is done by applying a transformation T to the original image data, then an inverse spatial transformation T' would be applied to the modified image mask to convert the modified image mask back to its original space prior to modifying the original image data based on the modified image mask.

FIGS. 15A-15D and 16A-16D illustrate examples of de-identified images generated according to an embodiment of the present invention. Shown in FIGS. 15A-15D are 3D views of skin surface reconstructions from four different medical images. The skin surface reconstructions in FIGS. 15A and 15B were generated from T1-weighted MRI images of two different patients; those in FIGS. 15C and 15D were generated from T2-weighted MM images of the same patients as in FIGS. 15A and 15B. FIGS. 16A-16D show skin-surface reconstructions generated from the same MM images as FIGS. 15A-15D, respectively, after applying an implementation of de-identification process 200 described above. As can be seen, the de-identified skin surfaces in FIGS. 16A-16D are recognizable as faces, but patient-identifying details are obscured.

Figure 17:
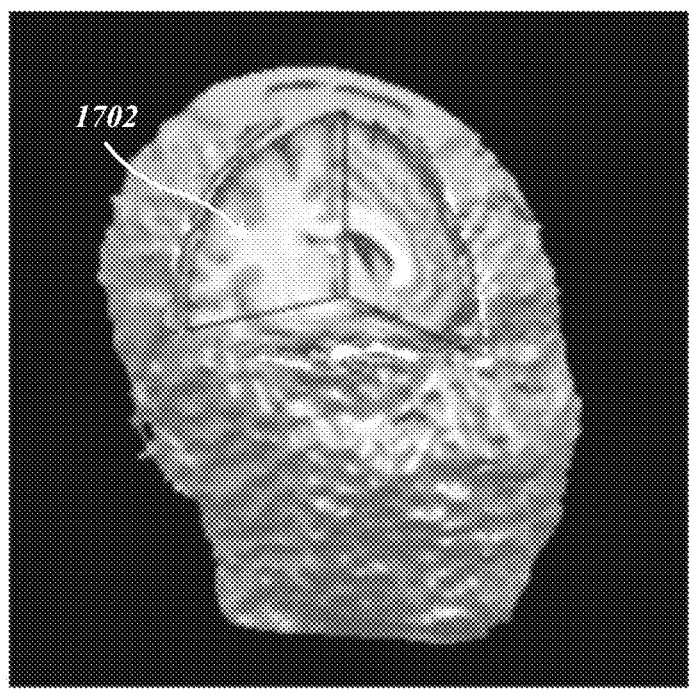
FIG. 17 shows a 3D cutaway view of a de-identified medical image generated according to an embodiment of the present invention.

FIG. 17 shows a 3D cutaway view of a de-identified medical image generated according to an embodiment of the present invention. As shown in cutaway region 1702, details of the internal anatomical structure (in this case, the brain) are preserved in the de-identified medical image. Thus, the processes described herein can selectively alter the surface anatomical features in a medical image sufficiently to obscure a patient's identity without loss of information pertaining to internal anatomy. In some embodiments, the general shape of surface anatomy can be preserved; for instance, in FIG. 17, it is possible to see that the patient has eyes, a nose, and a mouth even though the shapes are distorted.

System Implementation

Data analysis and computational operations of the kind described herein can be implemented in computer systems that may be of generally conventional design, such as a desktop computer, laptop computer, tablet computer, mobile device (e.g., smart phone), or the like. Such systems may include one or more processors to execute program code (e.g., general-purpose microprocessors usable as a central processing unit (CPU) and/or special-purpose processors such as graphics processors (GPUs) that may provide enhanced parallel-processing capability); memory and other storage devices to store program code and data; user input devices (e.g., keyboards, pointing devices such as a mouse or touchpad, microphones); user output devices (e.g., display devices, speakers, printers); combined input/output devices (e.g., touchscreen displays); signal input/output ports; network communication interfaces (e.g., wired network interfaces such as Ethernet interfaces and/or wireless network communication interfaces such as Wi-Fi); and so on. De-identification processes described herein can be supported using existing application software such as MAT-LAB, Visual C++, other commercially-available development toolkits, or custom-built application software. Such software may be said to configure the processor to perform various operations, including operations described herein. In one specific implementation, a 3.2-GHz Intel Xeon® processor was able to execute the de-identification process described herein in a time of approximately 30 seconds per dataset, which is measurably faster than conventional de-identification processes.

Computer programs incorporating various features of the present invention may be encoded and stored on various computer readable storage media; suitable media include magnetic disk or tape, optical storage media such as compact disk (CD) or DVD (digital versatile disk), flash memory, and other non-transitory media. (It is understood that "storage" of data is distinct from propagation of data using transitory media such as carrier waves.) Computer readable media encoded with the program code may be packaged with a compatible computer system or other electronic device, or the program code may be provided separately from electronic devices (e.g., via Internet download or as a separately packaged computer-readable storage medium).

In alternative embodiments, a purpose-built processor may be used to perform some or all of the operations described herein. Such processors may be optimized for specific mathematical operations and may be incorporated into computer systems of otherwise conventional design or other computer systems.

In some embodiments, the hardware and/or software components to perform operations described herein can be incorporated into the medical imaging apparatus so that image data output from the apparatus is already de-identified. Alternatively, de-identification can be applied after the image data is transferred from the medical imaging apparatus to other storage.

Additional Embodiments

Embodiments described above provide systems and methods for de-identifying medical images. The de-identification is based on an image mask generated from the original medical image that is to be de-identified and does not require the use of any separate templates or maps. Processes as described can be performed without human intervention; for instance, there is no need to manually align a template to the image or correct errors in such alignment. In part because no templates or maps are required, the processes can be readily transferable to different imaging modalities and protocols. The processes are also computationally inexpensive, allowing for application to large datasets.

While the invention has been described with reference to specific embodiments, those skilled in the art will appreciate that variations and modifications are possible. All processes described above are illustrative and may be modified. Processing operations described as separate blocks may be combined, order of operations can be modified to the extent logic permits, processing operations described above can be altered or omitted, and additional processing operations not specifically described may be added. In some embodiments, the approximate skin surface generated using a process such as process 400 can be used directly in the modification stage (e.g., process 1200), without an additional refinement process (e.g., process 700).

De-identification processes described herein can be applied to medical images obtained using a variety of technologies. The medical images used for illustration were obtained using MIII, and those skilled in the art will appreciate that the same techniques can be applied to other medical images, including images obtained using CT scanning, or any other medical imaging technique that may provide data from which surface anatomical features of a patient could be reconstructed.

In addition, while the examples herein show de-identification processes applied to images of a patient's head and having the effect of obscuring facial features, it is to be understood that facial features may not be the only surface anatomical features that could be used to identify a patient. Accordingly, embodiments of the invention are not limited to images including heads or to de-identification of facial features; techniques described herein can be applied to de-identify images of any portion of a patient's body.

Thus, although the invention has been described with respect to specific embodiments, it will be appreciated that the invention is intended to cover all modifications and equivalents within the scope of the following claims.

What is claimed is:

1. A method of de-identifying a medical image, the method comprising:
    obtaining medical image data representing anatomy of a patient, the medical image data including a set of voxels defined in a three-dimensional space, each voxel having an original intensity value;
    analyzing the medical image data to generate an image mask that assigns each of the voxels to either a foreground region or a background region such that a skin surface at a boundary between the foreground region and the background region corresponds to one or more surface anatomical features of the patient;
    modifying the image mask by moving a randomly selected subset of voxels from the foreground region to the background region such that the skin surface is reshaped; and
    modifying the medical image data by assigning a uniform background intensity value to each voxel of the medical image data that is assigned to the background region of the modified image mask while preserving the original intensity values of each voxel of the medical image data that is assigned to the foreground region of the modified image mask.

2. The method of claim 1 wherein analyzing the medical image data to generate the image mask includes:
    identifying a largest connected region of low intensity voxels as belonging to a first approximate background region of a first approximate image mask; and
    identifying all other voxels as belonging to a first approximate foreground region of the first approximate image mask.

3. The method of claim 2 wherein analyzing the medical image data to generate the image mask further includes:
    applying a morphological correction to the first approximate background region; and
    modifying the first approximate image mask based on the morphological correction to produce a second approximate image mask that divides the voxels into a second approximate foreground region and a second approximate background region.

4. The method of claim 3 wherein analyzing the medical image to generate the image mask further includes:
    reconstructing an approximate skin surface from the second approximate image mask;
    identifying a set of super-voxels around the approximate skin surface; and
    for each super-voxel:
        determining whether the super-voxel includes at least a threshold number of voxels that are within the second approximate foreground region;
        assigning all voxels within the super-voxel to a refined foreground region of a refined image mask in the event that the super-voxel includes at least the threshold number of voxels that are within the second approximate foreground region; and
        assigning all voxels within the super-voxel to a refined background region of the refined image mask in the event that the super-voxel does not include at least the threshold number of voxels that are within the second approximate foreground region.

5. The method of claim 1 wherein modifying the image mask includes:
    randomly selecting a plurality of seed locations on the skin surface of the image mask; and
    for each seed location, applying a kernel at the seed location to select one or more voxels near the seed location to be moved from the foreground region to the background region of the image mask.

6. The method of claim 5 wherein the same kernel is applied at each seed location.

7. The method of claim 6 wherein the kernel is a spherical kernel.

8. The method of claim 5 wherein modifying the image mask further includes:
applying iterative Gaussian smoothing to propagate a deformation at each seed location.

9. The method of claim 1 wherein the medical image data is data produced from a magnetic resonance imaging (MM) scan of the patient.

10. A computer system comprising:
a storage medium to store medical image data representing anatomy of a patient, the medical image data including a set of voxels defined in a three-dimensional space, each voxel having an original intensity value; and
a processor coupled to the storage medium and configured to:
analyze the medical image data to generate an image mask that assigns each of the voxels to either a foreground region or a background region such that a skin surface at a boundary between the foreground region and the background region corresponds to one or more surface anatomical features of the patient;
modify the image mask by moving a randomly selected subset of voxels from the foreground region to the background region such that the skin surface is reshaped; and
modify the medical image data by assigning a uniform background intensity value to each voxel of the medical image data that is assigned to the background region of the modified image mask while preserving the original intensity values of each voxel of the medical image data that is assigned to the foreground region of the modified image mask.

11. The computer system of claim 10 wherein analyzing the medical image data to generate the image mask includes:
identifying a largest connected region of low intensity voxels as belonging to a first approximate background region of a first approximate image mask; and
identifying all other voxels as belonging to a first approximate foreground region of the first approximate image mask.

12. The computer system of claim 11 wherein analyzing the medical image data to generate the image mask further includes:
applying a morphological correction to the first approximate background region; and
modifying the first approximate image mask based on the morphological correction to produce a second approximate image mask that divides the voxels into a second approximate foreground region and a second approximate background region.

13. The computer system of claim 12 wherein analyzing the medical image to generate the image mask further includes:
reconstructing an approximate skin surface from the second approximate image mask;
identifying a set of super-voxels around the approximate skin surface; and
for each super-voxel:
determining whether the super-voxel includes at least a threshold number of voxels that are within the second approximate foreground region;
assigning all voxels within the super-voxel to a refined foreground region of a refined image mask in the event that the super-voxel includes at least the threshold number of voxels that are within the second approximate foreground region; and
assigning all voxels within the super-voxel to a refined background region of the refined image mask in the event that the super-voxel does not include at least the threshold number of voxels that are within the second approximate foreground region.

14. The computer system of claim 10 wherein modifying the image mask includes:
randomly selecting a plurality of seed locations on the skin surface of the image mask; and
for each seed location, applying a kernel at the seed location to select one or more voxels near the seed location to be moved from the foreground region to the background region of the image mask.

15. The computer system of claim 14 wherein the same kernel is applied at each seed location.

16. The computer system of claim 15 wherein the kernel is a spherical kernel.

17. The computer system of claim 14 wherein modifying the image mask further includes:
applying iterative Gaussian smoothing to propagate a deformation at each seed location.

18. The computer system of claim 10 wherein the medical image data is data produced from a magnetic resonance imaging (MRI) scan of the patient.

19. A computer-readable storage medium having stored therein program instructions that, when executed by a processor of a computer system, cause the processor to execute a method comprising:
obtaining medical image data representing anatomy of a patient, the medical image data including a set of voxels defined in a three-dimensional space, each voxel having an original intensity value;
analyzing the medical image data to generate an image mask that assigns each of the voxels to either a foreground region or a background region such that a skin surface at a boundary between the foreground region and the background region corresponds to one or more surface anatomical features of the patient;
modifying the image mask by moving a randomly selected subset of voxels from the foreground region to the background region such that the skin surface is reshaped; and
modifying the medical image data by assigning a uniform background intensity value to each voxel of the medical image data that is assigned to the background region of the modified image mask while preserving the original intensity values of each voxel of the medical image data that is assigned to the foreground region of the modified image mask.

20. The computer-readable storage medium of claim 19 wherein analyzing the medical image data to generate the image mask includes:
identifying a largest connected region of low intensity voxels as belonging to a first approximate background region of a first approximate image mask; and
identifying all other voxels as belonging to a first approximate foreground region of the first approximate image mask.

21. The computer-readable storage medium of claim 20 wherein analyzing the medical image data to generate the image mask further includes:
applying a morphological correction to the first approximate background region; and
modifying the first approximate image mask based on the morphological correction to produce a second approximate image mask that divides the voxels into a second approximate foreground region and a second approximate background region.

22. The computer-readable storage medium of claim 21 wherein analyzing the medical image to generate the image mask further includes:

reconstructing an approximate skin surface from the second approximate image mask;

identifying a set of super-voxels around the approximate skin surface; and for each super-voxel:

determining whether the super-voxel includes at least a threshold number of voxels that are within the second approximate foreground region;

assigning all voxels within the super-voxel to a refined foreground region of a refined image mask in the event that the super-voxel includes at least the threshold number of voxels that are within the second approximate foreground region; and assigning all voxels within the super-voxel to a refined background region of the refined image mask in the event that the super-voxel does not include at least the threshold number of voxels that are within the second approximate foreground region.

23. The computer-readable storage medium of claim 19 wherein modifying the image mask includes:

randomly selecting a plurality of seed locations on the skin surface of the image mask; and for each seed location, applying a kernel at the seed location to select one or more voxels near the seed location to be moved from the foreground region to the background region of the image mask.

24. The computer-readable storage medium of claim 23 wherein the same kernel is applied at each seed location.

25. The computer-readable storage medium of claim 24 wherein the kernel is a spherical kernel.

26. The computer-readable storage medium of claim 23 wherein modifying the image mask further includes:

applying iterative Gaussian smoothing to propagate a deformation at each seed location.

27. The computer-readable storage medium of claim 19 wherein the medical image data representing anatomy of a patient is obtained from a data storage medium of the computer system.

28. The computer-readable storage medium of claim 19 wherein the medical image data representing anatomy of the patient is obtained by performing a scan of the patient.

29. The computer-readable storage medium of claim 28 wherein the scan is a magnetic resonance imaging (MRI) scan.

* * * * *